United States Patent [19]

Fleischman

[11] Patent Number: 4,574,642

[45] Date of Patent: Mar. 11, 1986

[54] APPARATUS FOR AUTOMATED CRACK GROWTH RATE MEASUREMENT

[75] Inventor: Thomas S. Fleischman, North Canton, Ohio

[73] Assignee: The Firestone Tire & Rubber Company, Akron, Ohio

[21] Appl. No.: 674,437

[22] Filed: Nov. 23, 1984

[51] Int. Cl.⁴ .................................... G01N 21/88
[52] U.S. Cl. ................................ 73/799; 73/800
[58] Field of Search .......................... 73/799, 800

[56] References Cited

U.S. PATENT DOCUMENTS

| | | | |
|---|---|---|---|
| 3,918,299 | 11/1975 | Donnadieu | 73/799 |
| 3,983,745 | 10/1976 | Juusola | 73/799 |
| 4,003,246 | 1/1977 | Cain | 73/799 |
| 4,175,447 | 11/1979 | Fukuhara | 73/799 |
| 4,418,563 | 12/1983 | Kalthoff et al. | 73/799 |

FOREIGN PATENT DOCUMENTS

| | | | |
|---|---|---|---|
| 211626 | 12/1983 | Japan | 73/799 |
| 2057124 | 3/1981 | United Kingdom . | |
| 2108684 | 5/1983 | United Kingdom . | |

OTHER PUBLICATIONS

Ind. Lab. (U.S.A.), vol. 38, No. 2 (Feb. 1972), Burnos et al.

Primary Examiner—Stewart J. Levy
Assistant Examiner—Hezron E. Williams
Attorney, Agent, or Firm—Ernst H. Ruf

[57] ABSTRACT

Apparatus for monitoring and measuring the growth of a crack in an elastic specimen. The specimen is repeatedly flexed by a piston at a set frequency and periodically slowed to a substantially lower frequency during which time a line scan camera monitors the length of the crack. The camera is positioned such that the specimen is drawn through the scan line thereof. The camera is calibrated such that the output signal from the camera correlates directly to the cracklength. This output signal is digitized, received, and stored by a digital processor for use in determining the crack growth rate.

17 Claims, 6 Drawing Figures

APPARATUS FOR AUTOMATED CRACK GROWTH RATE MEASUREMENT

TECHNICAL FIELD

The invention herein resides in the art of testing apparatus, and more particularly to such apparatus for testing elastomeric materials such as rubber whereby the fatigue crack propagation may be monitored and measured.

BACKGROUND OF THE INVENTION

In the past, it has been desirable to make life predictions on products made of rubber and other low modulus materials. Such materials may be tested to determine the resistance of the material to cracks or crack propagation. Typically, a strip of the material is placed into a reciprocating device such as a mechanical or servohydraulic testing machine. The strip is slit or precracked at an edge thereof and then repeatedly flexed or stretched a predetermined amount, with periodic measurements of the growth of the slit or crack being manually taken. From these measurements, the crack growth rate could be determined.

In the past, the periodic measurements were taken visually by an operator through a microscope or other optical device appropriately equipped with a reticle. The growth of the crack was thereby monitored and recorded as a function of the number of flexing cycles imparted to the sample or specimen. The growth of the crack length as a function of the number of flexing cycles could then be plotted. The derivative of this curve is then the growth rate, from which the resistance of the material to crack growth may be determined in a well known fashion.

In the prior art, the operation has been totally manual, relying upon an operator to physically start or stop the reciprocating device, visually observe the length of the crack in the specimen, determine the number of cycles between measurements, determine the crack growth from the last measurement, and ascertain the crack growth rate. Being totally manual, the prior art approach has been time consuming and given to inaccuracies resulting from the subjective operator readings with their inherent human error. The prior test could not be run continuously without the presence of operators over a number of sequential shifts. When the tests were run discontinuously, the results were suspect due to resultant viscoelastic transient effects.

There have been attempts at automating methods of monitoring crack growth in a specimen. Applicant is aware of U.S. Pat. No. 4,175,447 which teaches the use of reflected light rather than transmitted light to characterize a center cracked specimen. Applicant is concerned with edge-cracked specimens, monitored with transmitted light, and with particular means for following both the apex and mouth of the crack. Such is absent in this reference. Similarly, applicant is aware of British Pat. No. 2,057,124 which uses two-dimensional video mounted on a traveling base which is adapted to move parallel to the crack line. The reference fails, however, to teach a single dimensional stationary monitoring system and similarly fails to follow both the apex and mouth of the crack.

U.S. Pat. No. 4,418,563 is of general interest, but it incorporates a test method using caustics rather than transmitted light and is not particularly adapted for automated crack growth measurement. Pat. No. 3,918,299 presents a method of detecting cracks by utilizing eddy currents rather than optical techniques and, in that regard, is of general interest only. Pat. No. 3,983,745 uses displacement and force transducers to inferentially determine crack length, but is only functional for elastic materials, not the time dependent or viscoelastic materials of concern herein. Similarly, British Pat. No. 2,108,684 uses light reflected off an applied coating for testing cracks in stiff elastic materials and is not adapted for the concept presented herein. Finally, an article by Burnos, et al appearing on page 305 of Ind. Lab (U.S.A.), Vol. 3, No. 2 (Feb. 1972) is of very general interest, teaching the production of maximum sharpness stress concentration notches in cylindrical specimens. The concepts presented in this article are not fatigue related, nor are they for monitoring time dependent crack growth.

DISCLOSURE OF INVENTION

In light of the foregoing, it is an aspect of the invention to provide an apparatus for automated crack growth rate measurement which reduces operator errors and bias in the test procedure.

Another aspect of the invention is the provision of apparatus for automated crack growth rate measurement which is substantially unlimited with respect to data collection intervals.

A further aspect of the invention is the provision of apparatus for automated crack growth rate measurement which requires less manpower and downtime of the test equipment than previously known devices and techniques.

Still a further aspect of the invention is the provision of apparatus for automated crack growth rate measurement which allows greater and more accurate control of test variables than previously known devices.

Yet an additional aspect of the invention is the provision of apparatus for automated crack growth rate measurement which is readily constructed from state of the art elements.

The foregoing and other aspects of the invention which will become apparent as the detailed description proceeds are achieved by apparatus for monitoring the growth of a crack in the edge of an elastic specimen, comprising: first means for receiving and flexing the specimen; second means in juxtaposition to said first means for optically viewing the specimen in an area including the crack and generating an output signal; and third means connected to said second means for collecting and storing data obtained from said output signal.

Other aspects of the invention are attained by apparatus for monitoring the growth of a crack propagating from the edge of an elastic specimen, comprising: reciprocating means for receiving and flexing the specimen; a line scan camera maintained opposite said reciprocating means and having a scan line traversing an edge of the specimen; and processing means connected to said reciprocating means and said camera for controlling the frequency at which the specimen is flexed and periodically receiving data from said camera.

DESCRIPTION OF THE DRAWINGS

For a complete understanding of the objects, techniques and structure of the invention reference should be had to the following detailed description and accompanying drawings wherein.

BEST MODE FOR CARRYING OUT THE INVENTION

Figure 1:
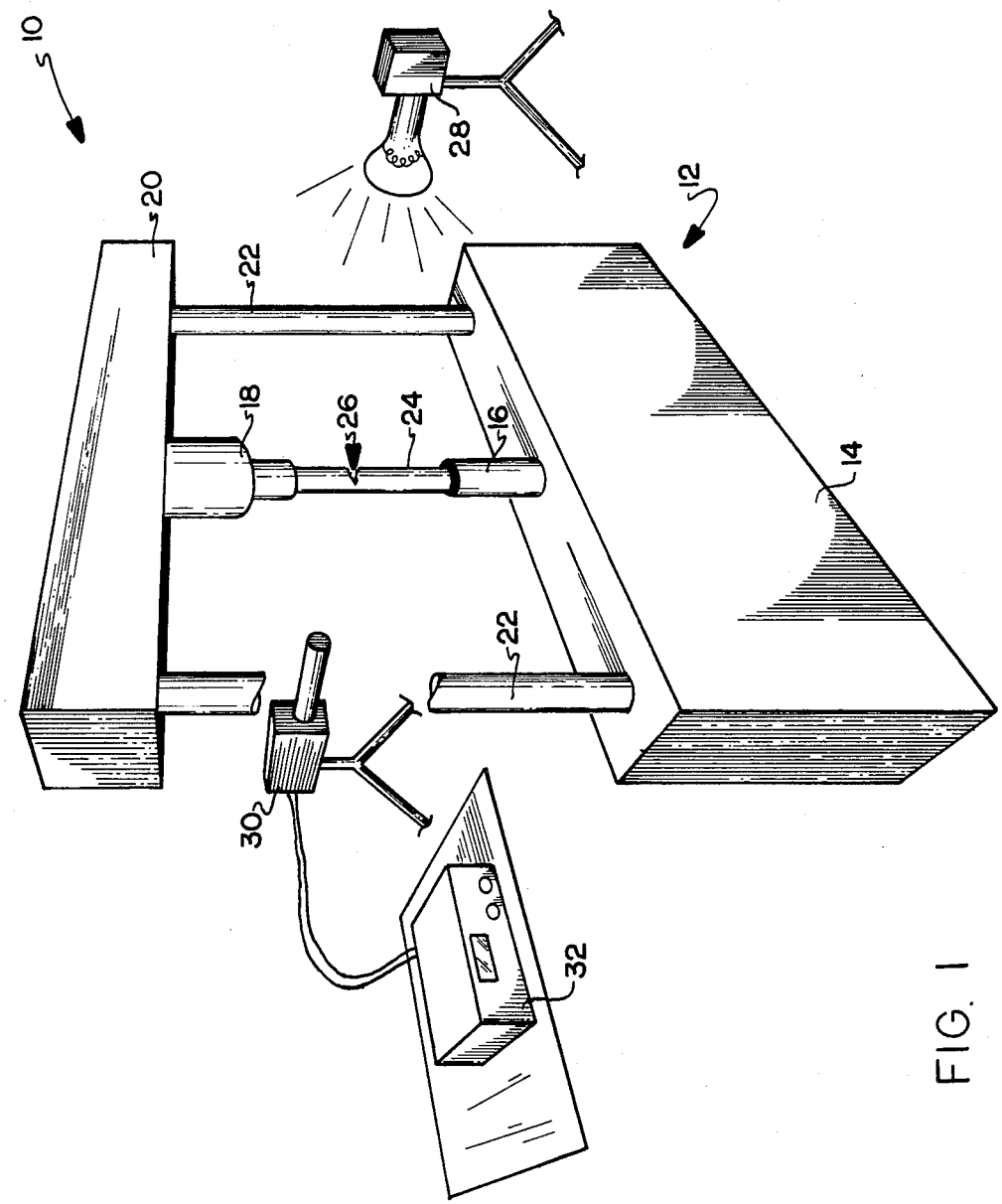
FIG. 1 is an illustrative perspective view of the apparatus of the invention showing the positioning of the light source and line scan camera.

Referring now to the drawings and more particularly FIG. 1, it can be seen that the crack growth rate measurement system of the invention is designated generally by the numeral 10. As shown, the system 10 includes a load frame 12, such as MTS Model 810 or 831, which would typically comprise a servo-hydraulic testing machine as is presently well known in the art. The load frame 12 includes an actuator 14 adapted for controlling a reciprocating piston 16. The stroke and frequency of the piston 16 is thereby regulated. A load cell or tranducer 18 is axially aligned with the piston 16 and positioned thereabove by being secured to the crosshead or header 20. Support columns or posts 22 interconnect the header 20 and actuator portion 14.

A sample or specimen of rubber or other elastomeric material is secured by clamps between the reciprocating piston 16 and the fixed load cell 18. The specimen 24 is characterized by an edge crack 26, the propagation of which is of concern under the test accomplished by the structure of the invention. The crack 26 is shown in greatly exaggerated proportions in the drawing of FIG. 1. In any event, a light source 28 is provided for backlighting the specimen 24 which, in the case of rubber, is black, giving a good contrast between the backlighting and the specimen. A line scan camera 30 is positioned on the opposite side of the specimen 24 from the light source 28 and collinear therewith. Preferably, the camera 30 may be a Model 300A as manufactured by Optron Corporation, having a resolution of 1024 pixels per scan. A camera controller 32, such as Model 300A as manufactured by Optron Corporation, converts the pixel information from the camera 30 into an analog signal proportional to the number of white pixels.

Figure 2:
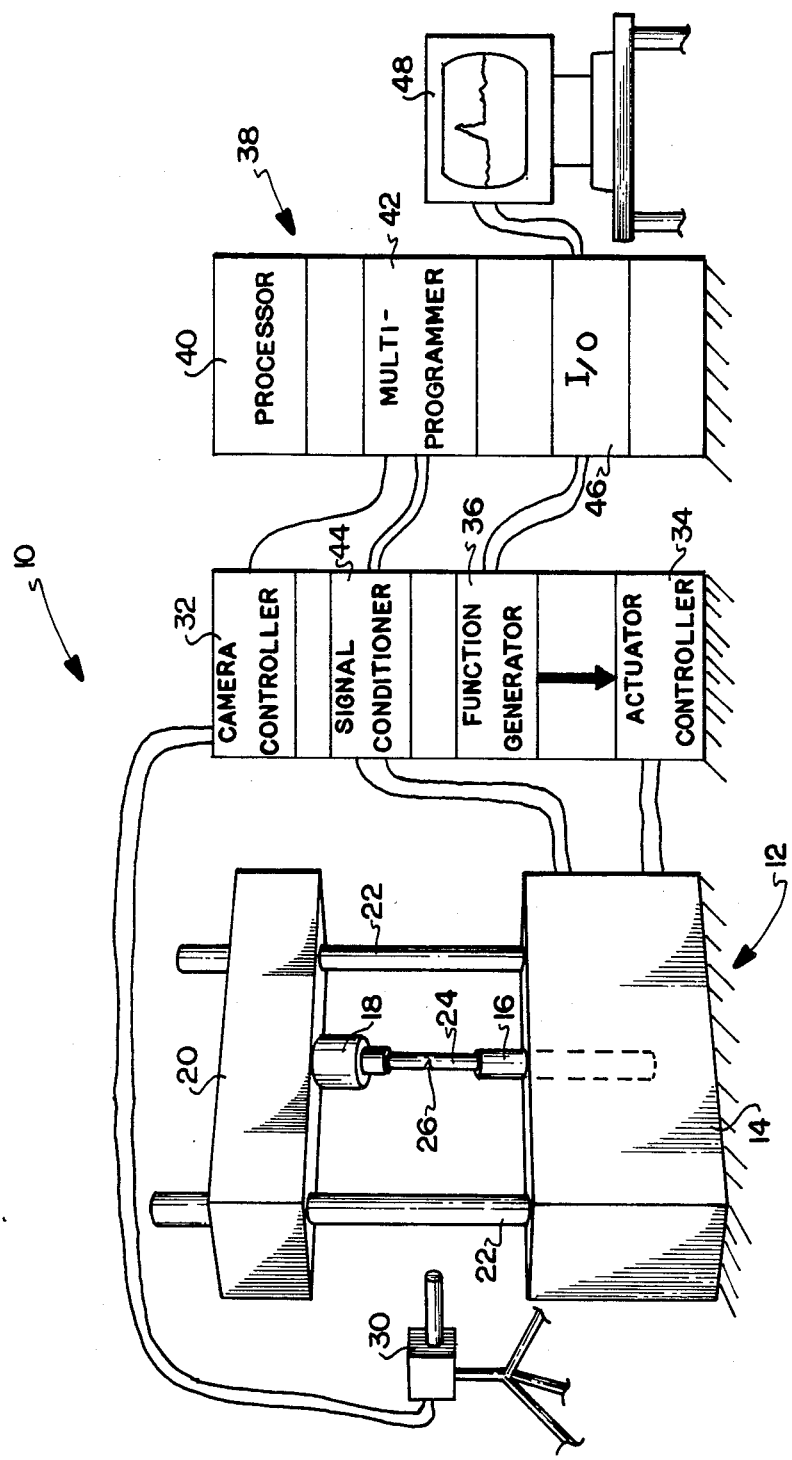
FIG. 2 is an illustrative perspective view of the apparatus of the invention showing the detailed elements thereof.

With reference now to FIG. 2, a more detailed illustration of the crack growth rate measurement system 10 may be seen. An actuator controller 34 interconnects with the actuator 14 to control the displacement and frequency of the stroke of the piston 16 to control the frequency and displacement throughout the test of the specimen 24. A programmable function generator 36 provides an analog signal to the controller 34 to achieve such control.

The heart of the control of the system 10 is the processing unit 38, including a digital processor 40 such as the Hewlett Packard HP1000 processor. The digital processor 40 interconnects through an input/output device 46 with the function generator 36, providing to the function generator 36 digital signals corresponding to the desired waveform, frequency and displacement of the stroke of the piston 16. The function generator 36 performs a digitial to analog conversion for application of the appropriate control signal to the controller 34.

Also included as a portion of the processing unit 38 is a multiprogrammer 42 such as the Hewlett Packard HP6942A. The multiprogrammer 42 includes an analog to digital converter to receive analog outputs of the line scan camera 30 via the camera controller 32, and subsequentially digitizing the same. This digitized output is then provided to the processor 40. Signal condition circuitry 44 is interposed between the load frame 12 and the multiprogrammer 42 for purposes of scaling the output signals from the load frame 12. The outputs from the load frame 12 consist principally of an output from a linear variable differential transformer (LVDT) indicating the displacement of the piston 16, and an output from the load cell 18 indicating the force imparted to the specimen 24 as it is flexed by the reciprocation of the piston 16. The signal condition circuitry 44 includes amplifiers for the purpose of amplifying or attenuating the outputs of the load frame 12 to a usable level by the multiprogrammer 42.

As mentioned above, an input/output device 46 provides for communication between the processor 40 and the function generator 36. The device 46 also allows for communication between the processor 40 and a graphics terminal 48 such as a Hewlett Packard HP2623A, consisting of a CRT on which may be displayed the output of the camera 30.

Figure 3:
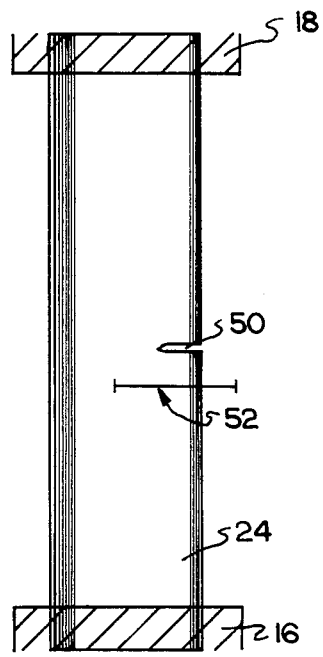
FIG. 3 is a front perspective view of a test specimen received by the apparatus of the invention.

As shown in FIG. 3, a rubber specimen 24, approximately 25 mm in width and 200 mm in length, is secured by clamps or the like between the reciprocating piston 16 and the fixed load cell 18. The specimen 24 is precracked as at 50 by means of cutting or slitting the same with a sharp instrument such as a razor blade. Typically, the length of the precrack 50 is approximately equal to the thickness of the specimen, for example 1 mm. The line scan camera 30 is positioned with the scan line 52 beneath the precrack 50. As can be seen, the scan line is of fixed length, extending from approximately the center of the specimen 24 to a point beyond the edge of the specimen 24 equivalent to approximately twenty percent of the total length of the scan line. As will be discussed hereinafter, as the crack 50 grows, the edges of the specimen 24 positioned on either side of the crack begin to deflect. This extension of the scan line 52 beyond the edge of the specimen 24 assures that such edge will always be within the scan line regardless of deflection. As will become further apparent, the scan line 52 is maintained below the precrack 50 such that the crack 50 is drawn through the scan line 52 when the specimen 24 is flexed as by reciprocating movement of the piston 16.

In operation, the specimen 24 is repeatedly flexed at a fixed frequency and displacement of the piston 16, controlled as presented above by the controller 34. After a selected number of such cycles, the processor 40 causes the actuator controller 34 to put out a signal by which the specimen 24 is extended very slowly, on the order of 0.1 hz, having a cycle period of 10 seconds. During this slow test cycle, the crack 26 is extended into and beyond the scan line 52 of the camera 30 and thence returned. During this test cycle, the processor 40 receives the output of the line scan camera 30 and measures the length of the crack 26 at that point in time in a manner to be discussed hereinafter.

At the beginning of each cycle, the function generator 36 puts out a sync signal. Upon the beginning of the slow test cycle, the sync signal enables the processor 40 to receive the output of the camera 30 via the camera controller 32. This output is digitized by the A/D converter of the multiprogrammer 42. The camera is enabled for the entire test cycle to obtain the output data shown in FIG. 5, to be discussed hereinafter. After obtaining the data from the test cycle, the frequency of the piston 16 is reinstated to the excitation frequency for crack propagation. Typically, such frequency is on the order of 3 hz. The specimen 24 is then cycled at this frequency for a selected number of cycles which has been determined to be sufficient for meaningful crack growth since the last monitoring. At that time, a test cycle is again entered with the piston 16 being slowed to 0.1 hz, and the processor 40 enabled to receive digitized signals from the camera 30 via the controller 32 and multiprogrammer 42. Hence, the growth of the crack 26 is monitored as a function of the number of cycles of flexing imparted to the specimen 24.

Figure 4:
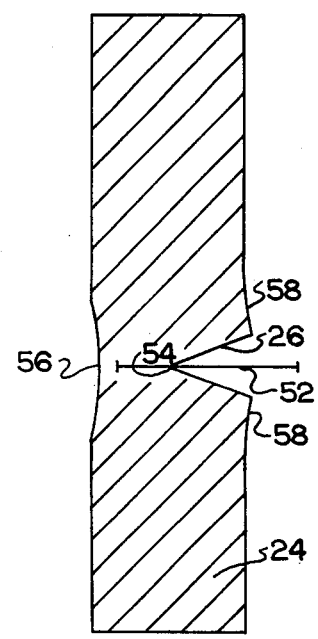
FIG. 4 is a front perspective view of a specimen in test according to the teachings of the invention.

As mentioned above, FIG. 4 presents a view of the specimen 24 during the test cycle in which data is taken by the processor 40. It will be noted that as the specimen 24 is stretched between the piston 16 and the stationary load cell 18, the crack 26 passes across the scan line 52 of the stationary camera 30. During the test cycle, the movement of the piston 16 actually draws the crack 26 from the position as shown in FIG. 3 below the crack to a substantially equal position above the crack and returns the same to the initial position. As shown in FIG. 4, the scan line 52 of the camera falls across the apex 54 of the crack 26.

Peculiarities of the specimen 24 may be noted in FIG. 4. For example, the specimen 24 curves inwardly or experiences in-plane deflection as at 56, at the back of the specimen 24 opposite the crack 26. This deflection is of a concave nature. In the same manner, the flexing of the specimen 24 results in convex deflection on each side of the crack 26 at the front of the specimen, forming lips as designated by the numeral 58. This in-plane deflection results from a weakening of the specimen 24 due to the presence of the crack 26. The actual length of the crack 26 at any point in time is accordingly the distance along the scan line from the apex 54 to the normal point on the scan lihe 52 taken from a maximum point of deflection 58. In other words, the deflection 56, 58 results in the crack 26 actually moving to the right as shown in FIG. 4. Accordingly, if the crack length were taken merely as the distance from the apex 54 to the line of the right edge of the specimen 24, the measurement would be inaccurate for failing to take into account the deflection of the specimen at the crack. Accordingly, the instant invention seeks to determine the crack length as the distance between the apex 54 and the point on the scan line 52 which would be intercepted by a line drawn between the points of maximum deflection 58 on each side of the mouth of the crack. Typically, this line would be normal to the scan line 52.

It should also be understood, with reference to FIG. 4, that the scan line 52 makes a transition from the totally dark field of the specimen 24 to the substantially light field resulting from the backlighting of the specimen by means of the light source 28. Accordingly, good resolution is achieved as to the point at which the specimen 24 ends and the crack 26 begins.

Figure 5:
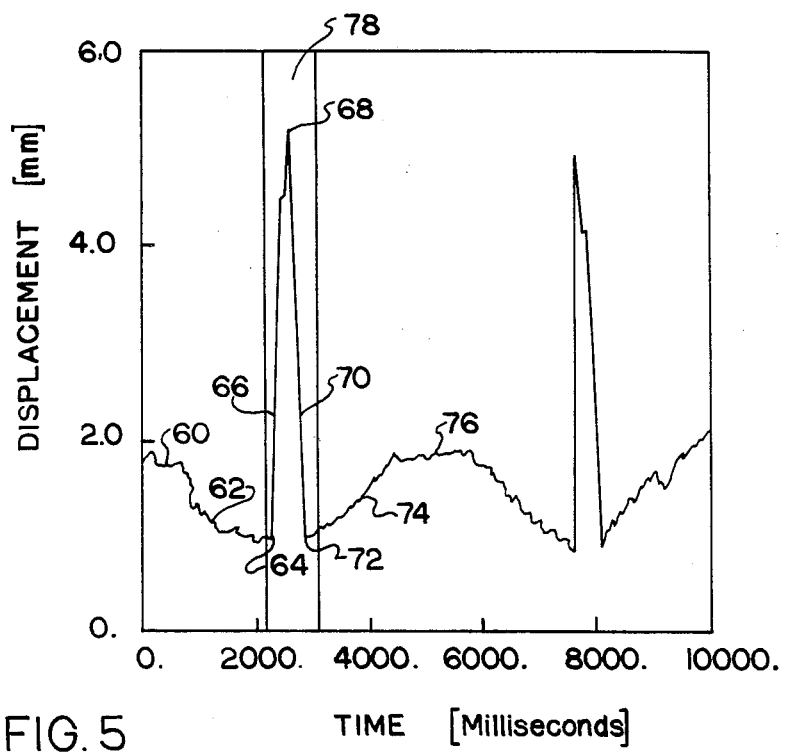
FIG. 5 is the output data characterizing the crack of the specimen during one test cycle.

With reference now to FIG. 5, a trace of the data obtained by the processor 40 during the 10 second cycle of the 0.1 hz test cycle is shown. It will be appreciated by those skilled in the art that the lens of the camera 30 is calibrated such that the camera output voltage correlates to the number of white pixels on the scan line 52. Each pixel correlates to a specific length. Accordingly, the voltage output of the camera 30 via the controller 32 correlates to the specific length along the scan line 52 which is characterized by white pixels.

As shown in FIG. 5, the output of the camera 30 has a quiescent level of approximately 2.0 mm. This correlates to the extension of the scan line 52 beyond the right edge of the specimen 24 as shown in FIG. 3. At the start of the cycle, as shown in FIG. 3, the number of black pixels is significant since the major portion of the scan line 52 is across the black specimen 24. As the specimen 24 is extended, the number of black pixels increases as at 62 due to the deflection of the specimen as at the lips 58, shown in FIG. 4. The number of black pixels hits the maximum as at 64 corresponding to the maximum point of deflection of the specimen 24 which would be that edge of the specimen immediately adjacent the opening or mouth of the crack 26. As the crack 26 comes into the scan line the number of white pixels begins to increase dramatically as at 66 to a maximum at 68, corresponding to an in-line relationship between the scan line 52 and the apex 54. As the specimen is further extended by the piston 16 beyond the apex 54, the number of light pixels decreases as at 70 to a mimimum as at 72, again due to the deflection at the upper lip 58 on the top side of the crack 26 as shown in FIG. 4. The number of black pixels then decreases as at 74, again due to the deflection 58, to the quiescent state 76, completing the first half of this test or monitoring cycle. On the upward stroke of the piston 16, the trace of FIG. 5 repeats itself for the reasons just described such that the second half of the cycle is a mirror image of the first half.

The in-line deflection and resultant movement of the lips 58, as just described, effectively shifts the crack 26 to the right as shown in FIG. 4. Accordingly, if one merely monitored the position of the apex 54 to determine cracklength and growth rate, the measurements would be in error by an amount dependent upon the degree of shift of the apex as a result of in-plane deflection. Such error has been found to be on the order of twenty percent.

The processor 40 is set to take data from the spike defined by the points 64–72, this spike corresponding to the length of the crack 26 at the time of measurement. To do this, the processor 40 defines a band 78 which encompasses the spike of interest. The processor 40 may establish the band 78 by taking the difference of overlapping groups of data points, finding where the difference increases greatly such as at 64–72, and then setting the band on either side of these points. In other words, the location for the band may be determined by maximizing the sum of the absolute differences of the displacement data for adjacent points. Of course, the band 78 could also be established by taking the derivative of the curve established by the data points and determining where that derivative or slope greatly increases. It should be appreciated that the band 78 is established to preclude anomalous minimum points in the trace of FIG. 5 resulting from buckling of the specimen 24 as by out-of-plane-deflection during flexure of the specimen.

Having established the band 78, the processor 40 establishes the length of the crack 26 for that particular test by determining the absolute length thereof as the maximum amplitude distance of separation between data points in the band 78. For example, the length of the crack in FIG. 5 would be determined on the basis of the measurement from the peak 68 to the trough 72.

Typically, the points 64, 72 would lie on the same horizontal line, but signal noise may account for a slight difference between the two. In any event, such a measurement guarantees that the measurement of the length of the crack 26 is unaffected by the deflection 58.

The length of the crack monitored at each test is recorded, as is the number of cycles or time elapsed between monitoring tests, such that the growth of the crack can be readily determined.

Figure 6:
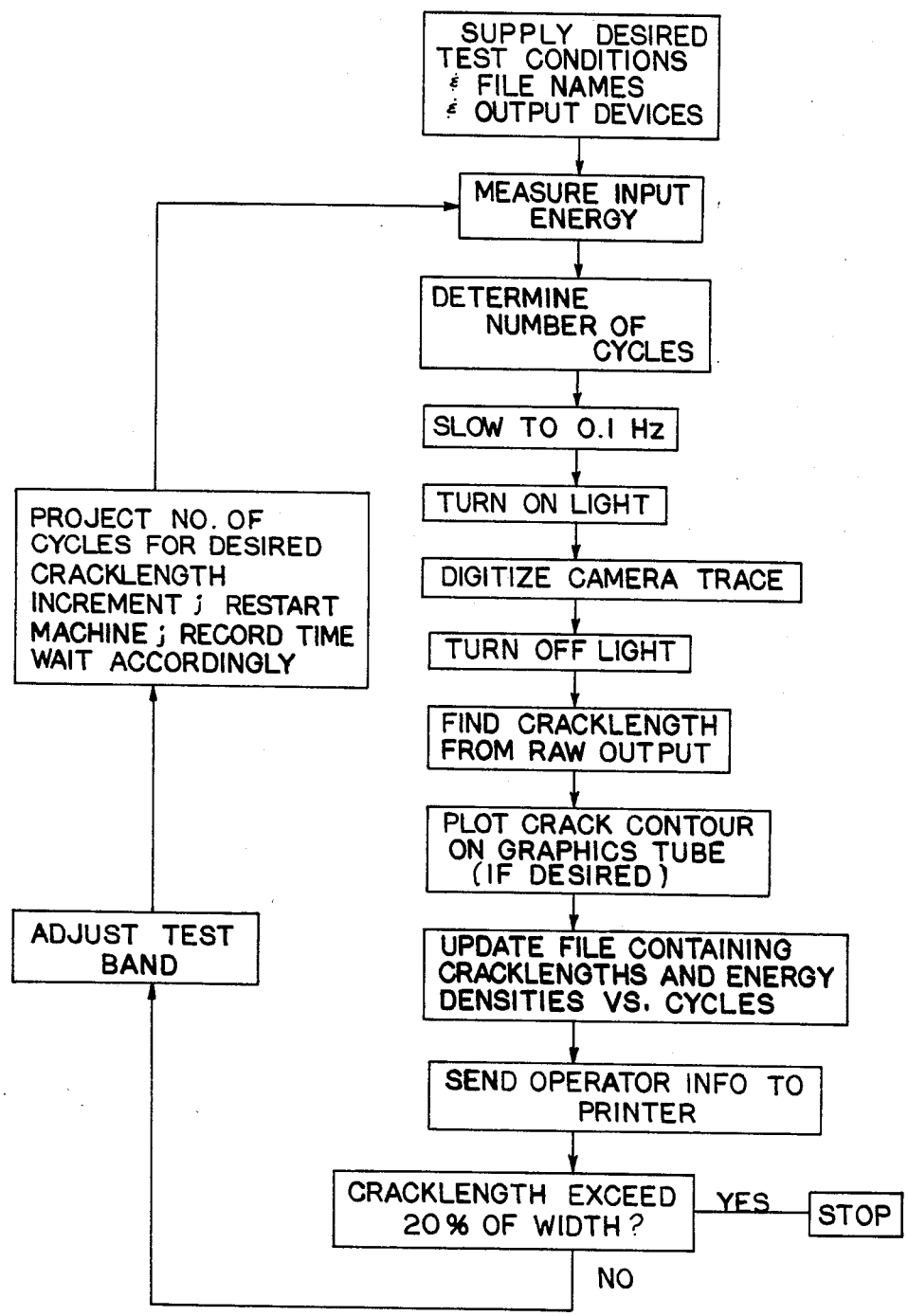
FIG. 6 is a flow chart demonstrating the technique of the invention.

With reference now to FIG. 6, the control program of the processor 40 may be seen in flow chart form. As demonstrated, the operator begins by providing to the processor 40 the conditions of the test such as the identity of the material, the test temperature, the specimen number, a frequency at which the piston 16 is to reciprocate, and the waveform output of the function generator 36. Similarly, the files in which data is to be placed are named, and the output devices such as the graphics terminal 48 are identified.

The test is then initiated by measuring the input energy to the specimen 24. As is well known in the art, the input energy to the specimen is the area under the curve achieved by a plot of the load sensed by the load cell 18 and the displacement of the specimen 24 as determined by the stroke of the piston 16. The input energy is stored by the processor for use in graphically plotting the fatigue crack propagation resistance of the material by plotting the crack growth rate versus the energy release rate in a manner well known in the art. While the data acquired from the apparatus and method disclosed herein is used for determining the characteristic fatigue crack propagation resistance of the material, it is the method and apparatus used for acquiring the data which is of importance herein and not the actual calculation which is well known in the industry. In any event, it should be appreciated that to determine the fatigue crack propagation resistance of the material, the input energy to the material at the time of the measurement of the crack is important.

The system then determines the number of flexing cycles imparted to the specimen 24 since the beginning of the test or since the last crack growth measurement was made. The system is then slowed to the monitoring frequency of approximately 0.1 hz. The lamp 28 is energized through a relay contact in the multiprogrammer 42 and the trace of the camera is digitized as by the controller 32 and multiprogrammer 42 discussed above. This digitized trace is stored in the processor 40 for the ten second duration of the monitoring cycle at 0.1 hz. The light or lamp 28 is then turned off. With the voltage output of the camera controller 32 being a function of length, the crack length is determined in the method described above with respect to FIG. 5. If desired, the crack contour may then be displayed on the graphics terminal 48. The processor 40 then updates its storage positions in memory with respect to crack length, energy density, and number of cycles of specimen flexing. This information may then be printed out, if desired.

The test of the instant invention is set such that the test terminates when the length of the crack 26 exceeds 20% of the entire width of the specimen 24. Of course, any desired criteria for terminating the test may be selected. If the crack length does not exceed the preset threshold, the width of the test band 78 is adjusted to accommodate the expanding width of the growing crack 26. This adjustment may be accomplished in any of several manners as discussed above. With the test band having been set, the processor 40 projects the number of cycles necessary to achieve a desired crack length increment. The actuator 14 is restarted to flex the specimen 24 such desired number of cycles. The time period of such flexing is measured and multiplied by the frequency to determine when the requisite number of cycles have been accomplished. At that time, the input energy is again measured, the number of cycles determined, and the monitoring cycle is entered into to obtain new information as to the crack growth resulting from the recent number of flexures.

The device and apparatus just discussed is capable of automatically achieving crack growth measurements in a test specimen. The crack growth rate may then be determined in standard fashion and, having available the input energy to the specimen, the fatigue crack propagation resistance of the material may also be demonstrated. The foregoing test is accomplished with a minimum of operator interface and without the subjectivity of operator readings and control. The calibrated stationary camera 30 achieves reliable test measurements which have been found to closely track those measurements obtained through the utilization of a microscope fitted with a reticle as first described herein.

Thus it can be seen that the objects of the invention have been achieved by the structure and techniques presented hereinabove. While in accordance with the patent statutes only the best mode and preferred embodiment of the invention has been presented and described in detail, it is to be understood that the invention is not limited thereto or thereby. Accordingly, for an appreciation of the true scope and breadth of the invention reference should be had to the following claims.

What is claimed is:

1. Apparatus for monitoring the growth of a crack in a first edge of an elastic specimen, comprising:
   first means for receiving and flexing the specimen;
   second means in juxtaposition to said first means for optically viewing the specimen in an area including the crack and generating an output signal, said second means comprising a line scan camera and said output signal being a function of the contrast between light and dark in a scan line of said camera, said scan line extending beyond at least the first edge of the specimen; and
   third means connected to said second means for collecting and storing data obtained from said output signal.

2. The apparatus according to claim 1 wherein said first means comprises a reciprocating piston receiving a first end of the specimen and a load cell receiving a second end.

3. The apparatus according to claim 1 wherein said third means comprises a digital processor having a memory, said memory receiving and storing said data obtained from said output signal.

4. The apparatus according to claim 3 wherein said third means further comprised an analog to digital converter interposed between said line scan camera and said digital process for digitizing said output signal.

5. The apparatus according to claim 1 wherein said third means is further operatively connected to said first means for controlling the amplitude and frequency of said flexing.

6. The apparatus according to claim 5 wherein said third means is selectively enabled to receive said data from said output signal.

7. The apparatus according to claim 6 wherein said third means is enabled for a full cycle of said flexing at periodic intervals.

8. The apparatus according to claim 7 wherein said data is received from said output signal during one half of said full cycle.

9. Apparatus for monitoring the growth of a crack propagating from the edge of an elastic specimen, comprising:

reciprocating means for receiving and flexing the specimen;

a line scan camera maintained opposite said reciprocating means and having a scan line extending beyond the edge of the specimen from which the crack propagates; and processing means connected to said reciprocating means and said camera for controlling the frequency at which the specimen is flexed and periodically receiving data from said camera.

10. The apparatus according to claim 9 wherein said camera is fixedly positioned and said scan line is orthogonal to an axis along which said specimen is flexed.

11. The apparatus according to claim 10 wherein said flexing of the specimen draws the crack through said scan line.

12. The apparatus according to claim 10 wherein said reciprocating means comprises a piston maintained in juxtaposition to a load cell, the specimen being received and maintained between said piston and load cell.

13. The apparatus according to claim 10 wherein said processing means maintains said reciprocating means at a fixed frequency, periodically interrupting said frequency with a reduced frequency, said processing means receiving said data from said camera during said reduced frequency.

14. The apparatus according to claim 13 wherein said processing means comprises a digital processor, and wherein said camera emits an analog output signal corresponding to the contrast between light and dark along said scan line on each scan of the camera.

15. The apparatus according to claim 14 wherein said processing means further comprises an analog to digital converter, receiving and digitizing said analog output signal.

16. The apparatus according to claim 9 which further includes a light source positioned opposite said camera with the specimen interposed therebetween.

17. The apparatus according to claim 16 wherein said light source is connected to, and selectively energized by, said processing means.

* * * * *